United States Patent [19]

Patois et al.

[11] Patent Number: 5,763,655
[45] Date of Patent: Jun. 9, 1998

[54] PREPARATION OF PENTENOIC ACIDS VIA HYDROXYCARBONYLATION OF BUTADIENE

[75] Inventors: Carl Patois, Lyons; Robert Perron, Charly, both of France

[73] Assignee: R.P. Fiber & Resin Intermediates, Courbevoie Cedex, France

[21] Appl. No.: 635,493

[22] Filed: Apr. 22, 1996

[30] Foreign Application Priority Data

Apr. 20, 1995 [FR] France ................. 95 04949

[51] Int. Cl.$^6$ ................. C07C 51/14
[52] U.S. Cl. ................. 562/522
[58] Field of Search ................. 562/522

[56] References Cited

U.S. PATENT DOCUMENTS 3,579,551 5/1971 Craddock et al. ................. 562/522
3,816,489 6/1974 Craddock et al. ................. 562/522
4,000,170 12/1976 Forster et al. .

FOREIGN PATENT DOCUMENTS 2158171 6/1973 France .

*Primary Examiner*—Robert W. Ramsuer
*Attorney, Agent, or Firm*—Burns, Doane, Swecker & Mathis, L.L.P.

[57] ABSTRACT

Pentenoic acids are selectively prepared via hydroxycarbonylation of butadiene with carbon monoxide and water, at a temperature above 30° C., under a partial pressure of carbon monoxide, measured at 25° C., equal to or greater than 0.5 bar, in the presence of a catalytically effective amount of an iridium-based catalyst and an iodine-containing or bromine-containing promoter therefor, in a solvent medium, wherein the iodine or bromine/iridium molar ratio is less than or equal to 20/1 and the concentration by weight of water in the reaction mixture is less than or equal to 8%.

18 Claims, No Drawings

PREPARATION OF PENTENOIC ACIDS VIA HYDROXYCARBONYLATION OF BUTADIENE

BACKGROUND OF THE INVENTION

1. Technical Field of the Invention

The present invention relates to the preparation of pentenoic acids via hydroxycarbonylation of butadiene, by reacting same with carbon monoxide and water.

2. Description of the Prior Art

It is known to this art that one technique for the synthesis of adipic acid, one of the two basic starting materials for nylon 66, entails the double carbonylation of butadiene.

Although it is conceivable to conduct the two hydroxycarbonylation reactions to convert butadiene into adipic acid in a single step, in practice it transpires that these two reactions must be carried out successively, at least in part, if it is desired to attain selectivities which are sufficiently high to permit economically conducting the process on an industrial scale.

U.S. Pat. No. 3,579,551 describes a process for the conversion of a compound containing at least one ethylenic double bond into a carboxylic acid, by reaction with carbon monoxide and water, in the presence of an iridium compound and an iodine-containing promoter, at a temperature of 50° C. to 330° C. and under a partial pressure of monoxide of about 0.3 to 210 bar.

In the process described, it would appear that any iridium compound can be used and various types of iodine-containing compounds are exemplified; the iodine/iridium molar ratio may vary over a very wide range, from 1/1 to 2,500/1 and preferably from 3/1 to 300/1.

The reaction medium may contain any solvent compatible with the catalytic system, monocarboxylic acids having from 2 to 20 carbon atoms, such as acetic acid, propionic acid, hexanoic acid, decanoic acid, dodecanoic acid, naphthoic acid, oleic acid or trans-9-octadecenoic acid, being preferred.

The examples set forth in the '551 patent indicate that the process predominantly forms branched carboxylic acid. Thus, the hydroxycarbonylation of propylene principally forms isobutyric acid (Example 1) whereas the hydroxycarbonylation of 1-hexene principally forms branched C7 acids (Example 19).

U.S. Pat. No. 3,816,489, to the same inventors as the '551 patent and which follows directly therefrom, describes employing an iodine/iridium molar ratio of 3/1 to 100/1 in an attempt to predominantly obtain linear carboxylic acid. When applied to monoolefins such as 1- hexene, 1-pentene, 2-pentene and 1-dodecene, this technique appears to attain the desired result. No example in the '489 patent is carried out with a diene.

If, however, the process according to U.S. Pat. No. 3,759,551 is carried out in order to hydroxycarbonylate a diene such as butadiene, it is observed that the selectivity in respect of pentenoic acids, the desired final products, is very low or even zero and that the corresponding saturated acids, namely, valeric acid and methylbutyric acid, are essentially obtained.

EP-A-0,405,433 describes the hydroxycarbonylation of butadiene into pentenoic acids, in the presence of a rhodium catalyst and a bromide or iodide promoter, in a carboxylic acid solvent. This process employs a catalyst based on rhodium, which is a particularly expensive metal.

The difficulty of the hydroxycarbonylation of butadiene into pentenoic acids thus has not been resolved in an economically satisfactory manner by the techniques described in the prior art.

SUMMARY OF THE INVENTION

Briefly, the present invention features an improved process for the hydroxycarbonylation of butadiene, comprising reacting same with carbon monoxide and water, at a temperature above 30° C., under a partial pressure of carbon monoxide, measured at 25° C., equal to or greater than 0.5 bar, in the presence of a catalytically effective amount of an iridium-based catalyst and an iodine-containing or bromine-containing promoter therefor, in a solvent medium, wherein the iodine or bromine/iridium molar ratio is less than or equal to 20/1 and the concentration by weight of water in the reaction mixture is less than or equal to 8%.

DETAILED DESCRIPTION OF BEST MODE AND SPECIFIC/PREFERRED EMBODIMENTS OF THE INVENTION

More particularly according to the present invention, the concentration by weight of water in the reaction mixture preferably ranges from 0.00001% to 5%.

Even more preferably, the concentration by weight of water in the reaction mixture ranges from 0.01% to 2%.

In one preferred embodiment of the process of the invention, water is progressively injected as the reaction proceeds, thereby permitting its concentration in the reaction mixture to be maintained at a very low value, while at the same time permitting the hydroxycarbonylation reaction to be carried out.

The lower limit of the concentration of water is thus provided as exemplary only, since it may be very low at any given instant, in particular in the hypothesis indicated above of continuous injection of water, which is then rapidly converted.

The starting material substrate, butadiene, may contain a minor amount of derivative compounds, for example allylic butenols such as 3-buten-2-ol, 2-buten-1-ol and mixtures thereof.

Preferably, the butadiene constitutes at least 80% by weight of the butadiene/butadiene derivatives mixture and, even more preferably, at least 90%.

The concentration of butadiene in the mixture is also an important parameter to take into account when carrying out the process of the invention. It is preferably maintained at a value less or equal to 16% by weight relative to the total weight of the reaction mixture.

The concentration of butadiene may be instantaneously very low, in particular in the event of continuous injection of butadiene, which is then converted very rapidly. There is thus no critical lower limit for this concentration, which depends in particular on the mode of introduction of the butadiene.

Preferably, the concentration of butadiene in the reaction mixture is less than or equal to 11% on a weight for weight basis and, even more preferably, less than or equal to 5.5% on a weight for weight basis.

For the iridium catalyst required by the subject process, various sources of iridium may be used.

Exemplary such sources of iridium include the following:
Ir metal; $IrO_2$; $Ir_2O_3$;
$IrCl_3$; $IrCl_3 \cdot 3H_2O$;
$IrBr_3$; $IrBr_3 \cdot 3H_2O$;
iridium iodides;

iridium carboxylates, in particular Ir acetate or Ir pentenoate;

$Ir_2(CO)_4Cl_2$; $Ir_2(CO)_4I_2$;

$Ir_2(CO)_8$; $Ir_4(CO)_{12}$;

$Ir(CO) [P(C_6H_5)_3]_2I$;

$Ir(CO) [P(C_6H_5)_3]_2Cl$;

$Ir[P(C_6H_5)_3]_3I$;

$HIr[P(C_6H_5)_3]_3(CO)$;

$Ir(acac) (CO)_2$;

$[IrCl(cod)]_2$;

(acac=acetylacetonate; cod=1,5-cyclooctadiene).

The amount of catalyst to be employed may vary over a wide range.

In general, an amount, expressed as moles of iridium metal per liter of reaction mixture, ranging from $10^{-4}$ to $10^{-1}$ provides satisfactory results. Lower amounts may be used but it is observed, however, that the reaction rate is low. Larger amounts present no drawbacks other than from an economical point of view.

The concentration of iridium in the reaction mixture preferably ranges from $5 \times 10^{-4}$ to $5 \times 10^{-2}$ mol/liter.

In the context of the subject process, by the expression "iodine-containing" or "bromine-containing promoter" is intended hydrogen iodide, hydrogen bromide and organoiodine and organobromine compounds capable of generating hydrogen iodide and hydrogen bromide, respectively, under the reaction conditions. These organoiodine and organobromine compounds are more particularly alkyl iodides and alkyl bromides having from 1 to 10 carbon atoms, among which methyl iodide and methyl bromide are preferred.

Among the promoters, iodine-containing promoters are generally preferred.

The iodine or bromine/iridium molar ratio preferably ranges from 1/1 to 10/1.

More preferably, the iodine or bromine/iridium molar ratio ranges from 1/1 to 5/1.

The lower limit indicated for the iodine or bromine/iridium molar ratio is not critical for the reaction. This ratio may be less than 1; however, in such a case there are economic drawbacks, since some of the iridium is not activated and plays almost no catalytic role.

Another characteristic of the subject process is the presence of a solvent which is liquid under the conditions of the hydroxycarbonylation of butadiene.

This solvent may be very varied in nature. Carboxylic acids, aliphatic hydrocarbons, cycloaliphatic hydrocarbons, aromatic hydrocarbons, chlorinated aliphatic hydrocarbons, chlorinated cycloaliphatic hydrocarbons, chlorinated aromatic hydrocarbons, aliphatic ethers, aromatic ethers, mixed ethers or mixtures of a plurality of these solvents are particularly exemplary.

The carboxylic acids which may be used as solvents in the process of the invention are, in particular, monoacids or diacids such as aliphatic acids, which are saturated or unsaturated, and aromatic acids, having a maximum of 20 carbon atoms, insofar as they are liquid under the operating conditions of the reaction. Exemplary such carboxylic acids include acetic aid, propionic acid, butanoic acid, valeric acid, methylbutanoic acid, adipic acid, methylglutaric acid, ethylsuccinic acid, dimethylsuccinic acid, pentenoic acids, benzoic acid, phenylacetic acid or mixtures of a plurality of these acids. It may be advantageous to employ carboxylic acids which are formed in the reaction for the hydroxycarbonylation of butadiene, in particular pentenoic acids, methyl-2-butenoic acids, valeric acid, methylbutanoic acid, adipic acid, methylglutaric acid, ethylsuccinic acid and dimethylsuccinic acid, especially in the event of recycling of the reaction products and of the catalyst.

3-Pentenoic acid or mixtures of 3-pentenoic acid with 2-pentenoic acid and/or 4-pentenoic acid and/or other reaction byproducts are more particularly employed.

Exemplary of the hydrocarbons, chlorinated hydrocarbons and ethers which may be used include benzene, toluene, xylenes, chlorobenzenes, dichloromethane, dichloroethane, hexane, cyclohexane and diphenyl ether.

For industrial applications of the subject process, recyclings of the catalyst, of the promoter and of the unreacted butadiene may result in the introduction into the reaction medium of greater or lesser amounts of other compounds, in particular byproducts formed during the hydroxycarbonylation reaction, which are different from the carboxylic acids indicated above. Thus, butenes and gamma-valerolactone may also be present in the reaction mixture. According to this invention, these compounds will be considered as constituting a fraction of the solvent system.

The hydroxycarbonylation reaction may be carried out at a temperature generally ranging from 60° C. to 230° C. and preferably from 90° C. to 200° C.

The partial pressure of carbon monoxide, measured at 25° C., ranges from 0.5 bar to 300 bar. It preferably ranges from 2 bar to 200 bar and, even more preferably, from 5 bar to 150 bar.

As indicated above, the process of the invention may be carried out in a continuous or batchwise manner. According to the particular technique selected, it will thus be necessary to adapt the various operating conditions described above.

It is known to this art, in particular from European Patents Nos. 0,511,126 and 0,536,064, to hydroxycarbonylate pentenoic acids into adipic acid, in the presence of an iridium-based catalyst and an iodine-containing or bromine-containing promoter. By adapting the operating conditions to those described for this second carbonylation, it is possible to use the final reaction mixture, after it has been subjected to optional treatments, for the preparation of adipic acid.

In order to further illustrate the present invention and the advantages thereof, the following specific examples are given, it being understood that same are intended only as illustrative and in nowise limitative.

EXAMPLE 1

The following reagents were charged into a 125 ml autoclave:

| | |
|---|---|
| (i) [IrCl (cod)]$_2$ | 0.42 mmol of Ir |
| (ii) HI (aqueous 57% solution) | 0.84 mmol |
| (iii) butadiene | 2.56 g (47.4 mmol) |
| (iv) water | 0.88 g (48.9 mmol) |
| (v) dichloromethane | 66.25 g |

The autoclave was closed and connected to a carbon monoxide supply circuit. The pressure was increased to 60 bar of CO and the autoclave was heated to 160° C.

At this temperature, the pressure was adjusted to 100 bar by carbon monoxide and the test was continued for 4 hours (h) under these conditions.

At the completion of the test, the autoclave was cooled and the reaction mixture was assayed by gas chromatography. The final reaction mixture was homogeneous and light orange in color. It contained no tarry compounds.

The yields (RY) obtained correspond to the number of moles of compound formed per 100 mol of butadiene employed.

The following results were obtained:

| | |
|---|---|
| (a) RY of 3-pentenoic acid: | 25% |
| (b) RY of valeric acid: | 6% |
| (c) RY of methylbutanoic acid: | 2% |
| (d) RY of methylbutenoic acids: | 1% |
| (e) RY of butenes | 9% |

EXAMPLE 2

The procedure of Example 1 was repeated, but in 3-pentenoic acid as solvent, at 140° C. and under a pressure of 50 bar.

The HI/Ir molar ratio was 2.5; the initial water concentration was 1.8% weight/weight.

After maintaining the temperature for 4 h, cooling the reaction mixture and assaying (homogeneous, orange-colored final reaction mixture, with no presence of tarry compounds), the following results were obtained:

| | |
|---|---|
| (a) RY of 3-pentenoic acid: | 45% |
| (b) RY of valeric acid: | 2% |
| (c) RY of methylbutanoic acid: | 1% |
| (d) RY of gamma-valerolactone: | 4% |
| (e) RY of diacids containing 6 carbon atoms: | 19% |

EXAMPLE 3

The procedure of Example 1 was repeated, but in 3-pentenoic acid as solvent, at 140° C. and under a pressure of 200 bar.

The HI/Ir molar ratio was 2.5; the initial water concentration was 1.8% weight/weight.

After maintaining the temperature for 4 h, cooling of the reaction mixture and assaying (homogeneous, orange-colored final reaction mixture, with no presence of tarry compounds), the following results were obtained:

| | |
|---|---|
| (a) RY of 3-pentenoic acid: | 40% |
| (b) RY of valeric acid: | 2% |
| (c) RY of methylbutanoic acid: | 2% |
| (d) RY of gamma-valerolactone: | 5% |
| (e) RY of diacids containing 6 carbon atoms: | 22% |

COMPARATIVE EXAMPLE A

This comparative test was carried out according to Example 10 of U.S. Pat. No. 3,759,551.

The following reagents were charged into a glass bulb placed in a 125 ml autoclave:

| | |
|---|---|
| (i) $(NH_4)_2IrCl_6$ | 0.0478 g (0.108 mmol of Ir) |
| (ii) HI (aqueous 57% solution) | 2.74 g (12.2 mmol) |
| (iii) butadiene | 5.78 g (107 mmol) |
| (iv) water | 0.65 g (36 mmol) |
| (v) acetic acid | 20 cm$^3$ (21.8 g) |

The HI/Ir molar ratio was 113; the initial water concentration was 5.9% weight/weight.

After 17 h at 165° C. under 42 bar of carbon monoxide, the final reaction mixture was dark brown with a large amount of tarry deposit. 2.1 g of these tars were isolated. The liquid fraction was assayed by gas chromatography.

The following results were obtained:

| | |
|---|---|
| (a) RY of C5 acids: including: | 0.47% |
| (b) RY of 3-pentenoic acid: | 0.05% |

The amount of pentenoic acid formed was very low; the other C5 acids were essentially valeric acid and methylbutanoic acid.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of pentenoic acid, comprising hydroxycarbonylating butadiene with carbon monoxide and water, at a temperature above 30° C., under a partial pressure of carbon monoxide, measured at 25° C., equal to or greater than 0.5 bar, in the presence of a catalytically effective amount of an iridium-based catalyst and an iodine-containing or bromine-containing promoter therefor, in a solvent medium, wherein the iodine or bromine/iridium molar ratio is less than or equal to 20/1 and the concentration by weight of water in the reaction mixture is less than or equal to 8%.

2. The process as defined by claim 1, wherein the concentration by weight of water in the reaction mixture ranges from 0.00001% to 5%.

3. The process as defined by claim 1, wherein the concentration of butadiene in the reaction mixture is maintained at a value less than or equal to 16% by weight relative to the total weight of the reaction mixture.

4. The process as defined by claim 3, wherein the concentration of butadiene in the reaction mixture is less than or equal to 11% on a weight for weight basis.

5. The process as defined by claim 1, said iridium catalyst comprising Ir metal; $IrO_2$; $Ir_2O_3$; $IrCl_3$; $IrCl_3.3H_2O$; $IrBr_3$; $IrBr_3.3H_2O$; an iridium iodide; an iridium carboxylate; $Ir_2(CO)_4Cl_2$; $Ir_2(CO)_4I_2$; $Ir_2(CO)_8$; $Ir_4(CO)_{12}$; $Ir(CO)[P(C_6H_5)_3]_2I$; $Ir(CO)[P(C_6H_5)_3]_2Cl$; $Ir[P(C_6H_5)_3]_3I$; $HIr[P(C_6H_5)_3]_3(CO)$; $Ir(acac)(CO)_2$; or $[IrCl(cod)]_2$.

6. The process as defined by claim 1, wherein the amount of catalyst, expressed as moles of iridium metal per liter of reaction mixture, ranges from $10^{-4}$ to $10^{-1}$ mol/liter.

7. The process as defined by claim 1, said iodine-containing or bromine-containing promoter comprising hydrogen iodide, hydrogen bromide or organoiodine or organobromine compounds capable of generating hydrogen iodide and hydrogen bromide, respectively, under the conditions of the reaction.

8. The process as defined by claim 1, wherein the iodine or bromine/iridium molar ratio ranges from 1/1 to 10/1.

9. The process as defined by claim 1, carried out in a solvent, which is liquid under the conditions of reaction, comprising a carboxylic acid, an aliphatic hydrocarbon, a cycloaliphatic hydrocarbon, an aromatic hydrocarbon, a chlorinated aliphatic hydrocarbon, a chlorinated cycloaliphatic hydrocarbon, a chlorinated aromatic hydrocarbon, an aliphatic ether, an aromatic ether, a mixed ether, or mixtures thereof.

10. The process as defined by claim 1, wherein the hydroxycarbonylation reaction is carried out at a temperature ranging from 60° C. to 230° C.

11. The process as defined by claim 1, wherein the hydroxycarbonylation reaction is carried out under a partial pressure of carbon monoxide, measured at 25° C., ranging from 0.5 bar to 300 bar.

12. The process as defined by claim 2, said concentration of water ranging from 0.01% to 2%.

13. The process as defined by claim 4, said concentration of butadiene being less than or equal to 5.5% on a weight for weight basis.

14. The process as defined by claim 6, said amount of catalyst ranging from $5 \times 10^{-4}$ to $5 \times 10^{-2}$ mol/liter.

15. The process as defined by claim 8, said molar ratio ranging from 1/1 to 5/1.

16. The process as defined by claim 10, carried out at a temperature ranging from 90° C. to 200° C.

17. The process as defined by claim 11, carried out under a partial pressure of carbon monoxide ranging from 2 bar to 200 bar.

18. The process as defined by claim 17, carried out under a partial pressure of carbon monoxide ranging from 5 bar to 150 bar.

* * * * *